United States Patent [19]

Meier et al.

[11] Patent Number: 5,006,526
[45] Date of Patent: Apr. 9, 1991

[54] METHOD OF TREATING A VERTEBRATE ANIMAL TO REDUCE PLASMA TRIGLYCERIDES AND CHOLESTEROL LEVELS AND TO ALLEVIATE AND PREVENT ATHEROSCLEROSIS

[75] Inventors: Albert H. Meier; Anthony H. Cincotta, both of Baton Rouge, La.; Donn D. Martin, Arlington, Tex.

[73] Assignee: Louisiana State University, Baton Rouge, La.

[21] Appl. No.: 258,889

[22] Filed: Oct. 17, 1988

[51] Int. Cl.$^5$ .............. A61K 31/495; A61K 31/50; A61K 31/44
[52] U.S. Cl. .............................. 514/250; 514/288; 514/824
[58] Field of Search .............. 514/250, 288, 824

[56] References Cited

U.S. PATENT DOCUMENTS

| | | | |
|---|---|---|---|
| 3,074,847 | 1/1963 | Bigsby | 167/55 |
| 3,752,814 | 8/1973 | Fluckiger et al. | 260/268 |
| 3,752,888 | 8/1973 | Fluckiger et al. | 424/250 |
| 3,755,328 | 8/1973 | Stadler et al. | 260/268 |
| 3,772,299 | 11/1973 | Stadler et al. | 260/268 |
| 3,849,562 | 11/1974 | Richardson | 424/261 |
| 3,901,891 | 8/1975 | Fehr et al. | 260/268 |
| 3,922,347 | 11/1975 | Bach et al. | 514/288 |
| 4,054,660 | 10/1977 | Clemens et al. | 514/288 |
| 4,151,283 | 4/1979 | di Salle et al. | 424/261 |
| 4,219,555 | 8/1980 | Rucman | 514/288 |
| 4,239,763 | 12/1980 | Milavec et al. | 514/250 |
| 4,444,778 | 4/1984 | Coughlin | 514/288 |
| 4,659,715 | 4/1987 | Meier et al. | 514/288 |
| 4,749,709 | 6/1988 | Meier et al. | 514/288 |
| 4,783,469 | 11/1988 | Meier et al. | 514/288 |

FOREIGN PATENT DOCUMENTS

| | | | |
|---|---|---|---|
| 890369 | 5/1982 | Belgium | 514/250 |
| 3408730 | 10/1983 | Fed. Rep. of Germany | 514/288 |
| 2408350 | 3/1977 | France | 514/824 |
| 2105192 | 3/1983 | United Kingdom | 514/824 |

OTHER PUBLICATIONS

Goodman et al. "The Pharmacological Basis of Therapeutics", MacMillan Pub (1980) 6th ed.
Cecil "Textbook of Medicine" Seventh ed; Saunders Co. (1983).
The Merck Manual of Diagnosis and Therapy, 14th ed. (1982); pp. 917–919.
Dorland's Illustrated Medical Dictionary 25th ed. (1974); pp. 143 and 160.
Chem. Abstracts 106(23):188934s El–denshary et al. (1987).
Chem. Abstracts 107(19): 173318r Abu–Jayyab (1987).

Primary Examiner—Stanley J. Friedman
Assistant Examiner—Raymond J. Henley, III
Attorney, Agent, or Firm—Llewellyn A. Proctor

[57] ABSTRACT

A method for the treatment of conditions associated with atherosclerosis in vertebrate animals, particularly man. A prolactin-inhibiting compound administered to the animal exhibiting the atherosclerotic conditions, in dosage sufficient to decrease the total plasma cholesterol and total triglyceride levels, will over a sufficient period of time suppress atherosclerosis and reduce lipid plaques in the walls of the blood vessels of the animal. Exemplary of prolactin-inhibiting compounds are the ergot-related drugs 2-bromo-alpha-ergocryptine, 6-methyl-8 beta-carbobenzyloxy-aminomethyl-10 alpha-ergoline, 1,6-dimethyl-8 beta-carbobenzyloxy-aminomethyl-10 alpha-ergoline, 8-acylaminoergolenes, ergocornine, 9,10-dihydroergocornine, and D-2-halo-6-alkyl-8-substituted ergolines.

18 Claims, No Drawings

METHOD OF TREATING A VERTEBRATE ANIMAL TO REDUCE PLASMA TRIGLYCERIDES AND CHOLESTEROL LEVELS AND TO ALLEVIATE AND PREVENT ATHEROSCLEROSIS

FIELD OF THE INVENTION

This invention relates to a method for the treatment of conditions associateed with atherosclerosis in vertabrate animals, particularly man. Plasma cholesterol and triglyceride levels are lowered, and blood vessel plaques in vertebrate animals are reduced by administering to the animal a prolactin-inhibiting compound.

BACKGROUND OF THE INVENTION

Over the last several years there has been an increasing interest in the role of plasma cholesterol and lipoproteins in the causation of coronary artery disease. Studies regarding the concentrations of plasma cholesterol and triglyceride have received a great deal of publicity regarding their roles in the initiation of atherosclerosis. At high concentrations, these lipids tend to cross arterial cell wall membranes. The cumulative deposition leads to the formation of lipid plaques in the arterial wall which is indicative of an atherosclerotic condition.

Prolactin has recently been shown to have an important role in stimulating the synthesis of lipids in the liver. Suppression of prolactin secretion can block hepatic lipogenesis, and prolactin replacement has fully restored lipogenesis because some of the lipid in the blood is produced in the liver. We believed therefore, that there was a possibility that inhibition of prolactin secretion might also reduce plasma lipids.

Ergot-related prolactin-inhibiting compounds are known and have been administered to vertebrate animals. In U.S. Pat. No. 3,752,814 and U.S. Pat. No. 3,752,888, e.g., 2-bromo-alpha-ergocryptine and certain of its pharmaceutically acceptable acid addition salts and methods for their preparation are described in detail. It is recognized that these compounds are useful in inhibiting lactation, and they exhibit antifertility effects.

In accordance with U.S. Pat. No. 4,659,715 ergot-related prolactin-inhibiting compounds, e.g., 2-bromo-alpha-ergocryptine, are administered to vertebrate animals to decrease body fat stores without concomitant decrease in body weight, and in accordance with U.S. Pat. No. 4,747,709 these compounds are administered to decrease body fat stores, with concomitant loss in body weight.

Despite the considerable usage of the ergot-related prolactin-inhibiting compounds in having been administered in the past to vertebrates for one purpose or another, insofar as known, these compounds have never been viewed as possibly useful for the treatment of atherosclerosis. Various other compounds, or drugs, however, have been employed generally for such purpose; albeit none, insofar as known, have proven entirely satisfactory. One drug of this type is colestipal hydrochloride (Colestid) described in Chapter 21, at Page 224, under "Antilipemics" of "Nurses Guide to Drugs."

There exists a great need, and a tremendous interest by the scientific and medical communities, to develop pharmacological methods for treating vertebrate animals, especially humans, to suppress or to reverse, or both suppress and reverse, the formation of arterial lipid plaques in subjects, or victims to the atherosclerotic condition.

OBJECTS

It is, accordingly, the primary object of this invention to satisfy this need, and others.

In particular, it is an object of this invention to provide a pharmacological method for the treatment of a vertebrate animal, particularly a human, to decrease the total plasma cholesterol and total triglyceride levels in animals exhibiting, or diagnosed as having, undesirably high levels of these lipids and to reduce lipid plaques on the walls of the arteries and blood vessels of atherosclerotic subjects.

A further, and more specific objective is to provide a pharmacological method for decreasing the total plasma cholesterol and total triglyceride levels to suppress atherosclerosis and reduce arterial lipid plaques with minimal adverse side effects, if any.

THE INVENTION

These objects and others are achieved by administering to a vertebrate animal, or human, diagnosed as having an atherosclerotic condition, or the risk factors associated with the atherosclerotic condition (viz., high plasma cholesterol, or high plasma triglycerides, or both), a prolactin-inhibiting compound sufficient to decrease the total plasma cholesterol and total triglyceride levels in the blood, and over a period of time sufficient to reduce arterial lipid plaques in the walls of the blood vessels of said animal, or human. Thus, it has been found that a prolactin-inhibiting compound, notably an ergot-related prolactin-inhibiting compound, can be administered to a subject exhibiting the atherosclerotic condition, or diagnosed as having an atherosclerotic condition, to suppress the total cholesterol and total triglyceride levels in the blood, or plasma, of the subject. Such treatments will suppress the formation of arterial lipid plaques in the walls of the blood vessels, and continued over a sufficient period of time will reduce the arterial lipid plaques in the walls of the blood vessels of atherosclerotic subjects.

Studies, principally epidemiologic studies, have shown a direct relationship between coronary atherosclerotic disease and elevated cholesterol in the blood of humans. Whereas medical scientists, and practitioners, have not determined a precise total plasma cholesterol at which medical intervention is necessary in treating the disease, there are levels at which majority expert opinion would favor treatment of a subject. In general, when the total plasma cholesterol of a human subject exceeds about 200 mg/dl (milligrams/deciliter) the subject is diagnosed as having an atherosclerotic condition; and for purposes of this invention this level can be regarded as indicative of the atherosclerotic condition, or level at which a human subject would be diagnosed as having an atherosclerotic condition. The formation of lipid plaques in the arterial wall, at any level, is regarded as an atherosclerotic condition. In vertebrate animals other than human, the levels of total plasma cholesterol defining the atherosclerotic condition will differ and may be independently determined for each species. Total plasma cholesterol levels defining the atherosclerotic condition for Syrian hamsters should not exceed about 100 mg/dl, for pigs should not exceed about 100 mg/dl, Swiss Webster white mice should not exceed about 100 mg/dl, and for Zucker rats should not exceed about 100 mg/dl. The formation of lipid plaques in the arterial wall of the animal, at any level, is regarded as an atherosclerotic condition.

In the practice of this invention, when it is desirable to lower the total plasma cholesterol level of a subject, the total plasma triglyceride level of a subject, or both the total plasma cholesterol and total plasma triglyceride levels of a subject, a prolactin-inhibiting compound, notably an ergot-related prolactin-inhibiting compound, is administered to the subject in daily dosage amounts ranging from about 0.02 mg/kg body weight to about 6 mg/kg body weight. As a consequence a decrease will be observed in the total plasma cholesterol and triglyceride levels, generally at least about 15 percent, more generally from about 30 percent to about 50 percent. After treatment for at least about 25 days, preferably over a period ranging from about 90 days to about 180 days, it will be observed that there is no build up of lipid plaques in the walls of the blood vessels of the subject. Generally, after about 90 days, it becomes evident that the lipid plaques have decreased by at least 15 percent, generally at least 50 percent, and more generally by as much as 90 percent, based on weight, from that initially present. The ergot-related prolactin-inhibiting compound can be administered by injections (e.g., peritoneal, subcutaneous or intramuscular injections), implants or orally.

In its more preferred aspects an ergot-related prolactin-inhibiting compound is administered, particularly as relates to humans, in daily dosage ranging from about 2.0 mg/100 kg of body weight to about 10 mg/100 kg of body weight. As a result of these dosages the total plasma cholesterol and total plasma triglyceride levels will be reduced. If the dosages are continued for a period of at least 25 days, and preferably for a period ranging from at least about 90 days to about 120 days, there will result a decrease in the total plasma cholesterol and total plasma triglyceride levels of at least about 15 percent, and more generally from about 30 percent to about 50 percent. The build up of lipid plaques in the walls of the arteries and blood vessels of the subject will be abated, and by the end of the period of treatment, preferably after about 90 days the amount of plaque initially present will have decreased by as much as 15 percent, generally by as much as 50 percent, and more generally from about 50 percent to about 90 percent, based on weight.

Exemplary of prolactin-inhibiting, ergot-related compounds are: 2-bromo-alpha-ergocryptine; 6-methyl-8 beta-carbobenzyloxy-aminomethyl-10 alpha-ergoline; 1,6-dimethyl-8 beta-carbobenzyloxyaminomethyl-10 alpha-ergoline; 8-acylamino-ergolenes, such as 6-methyl-8 alpha-(N-acyl)amino-9-ergolene and 6-methyl-8 alpha-(N-phenylacetyl)amino-9-ergoline; ergocornine; 9,10-dihydroergocornine; and D-2-halo-6-alkyl-8-substituted ergolines, e.g., D-2-bromo-6-methyl-8-cyanomethylergoline. The foregoing ergot-related compounds and the processes for their formation are known to the art. From the standpoint of side effects, especially that on fertility, 2-bromo-ergo-cryptine has been found to be highly suitable for the practice of this invention.

The non-toxic salts of the prolactin-inhibiting ergot-related compounds formed from pharmaceutically acceptable acids are also useful in the practice of this invention.

When dosed with ergot-related compounds of this invention different animal species exhibit dissimilar sensitivities to prolactin-inhibition. Hence, when considering all species of vertebrate animals as a single group, the dosages required of this inveniton vary over a fairly wide range. Thus, the suitable dosage range is best determined empirically for each animal species. Generally, the minimum dosage needed to obtain the effect sought will be the preferred dosage as the chance of unwanted side effects is diminished and the cost of dosing will be kept to a minimum.

Capsules or tablets containing the unit doses of the ergot-related compounds are suitable for oral dosing. Generally, the ergot-related compounds will be used as a pharmaceutically acceptable salt when administered orally. If peritoneal dosing is used, the ergot-related compound will be provided with conventional sterile diluents, such as, mannitol, sucrose, vegetable oil, etc. The duration of administration may vary from species to species but is as long as is needed to obtain the effect sought. Generally, dosing should be administered in amounts to reduce plasma lipid levels and will be required for at least 25 days, and preferably longer, to substantially reduce lipid plaque deposits.

The following non-limiting examples are illustrative of the invention, and bring out its more salient features.

EXAMPLE I

In this example, the effects of bromocriptine (2-bromo-alpha-ergocryptine) treatment on plasma cholesterol concentration were examined in Syrian hamsters. Mature (6–8 months old) Syrian hamsters (body weight: 100–125 g) were caged in pairs, fed normal rodent feed ad libitum, maintained at 23° C. and provided 14-hour daily photoperiods (light onset: 0800). The hamsters were injected (i.p.) in equal doses twice daily at 0800 and 2000 with bromocriptine (60 ug/0.1 ml peanut oil/day) or peanut oil (controls); this corresponding to 0.6 mg/kg of body weight. After 14 days of treatment, the animals were anesthetized (sodium phenobarbital) and blood taken for analysis of plasma cholesterol according to Sigma Diagnostic Bulletin No. 351 (1986). The bromocriptine treatment reduced the plasma cholesterol concentration by 17% compared with control levels. Reference is made to Table I.

EXAMPLE II

Female pigs (200–250 lbs) were implanted with commercially available bromocriptine pellets in an ear said to release 10 mg/day. The pigs were maintained under normal outdoor conditions and ad libitum feeding. Feed consumption was not significantly altered by bromocriptine. After 4 weeks blood samples were taken near sunset for analysis of cholesterol. Bromocriptine treatment reduced the plasma cholesterol concentration by 13% compared with control levels. Reference is made to Table 1.

TABLE 1

| Bromocriptine Effects on Plasma Cholesterol Concentrations (mg/100 ml) in Hamsters[1] and Pigs.[2] | | |
|---|---|---|
|  | Hamsters | Pigs |
| Controls | 70 ± 2 (7)[3] | 100 ± 3 (12) |
| Bromocriptine | 58 ± 1 (6)[a] | 87 ± 3 (12)[b] |

[1]Syrian Hamsters (adult) received twice-a-day injections (i.p.) of bromocriptine in peanut oil for 14 days when blood samples were taken for cholesterol determination.
[2]Female pigs (200–250 lbs) were implanted with bromocriptine pellets (releasing 10 mg/day). Blood samples taken after 4 weeks near sunset for analysis of cholesterol.
[3]Mean ± Standard error of the mean; number of animals in parenthesis.
[a,b]Statistically different from controls ($p < 0.01^a$ and $p < 0.05$; Students' t).

EXAMPLE III

Mature (one year old) female Swiss Webster white mice were maintained at 23° C. and on a 14-hour daily photoperiod (0600–2000). The mice were injected (i.p.) daily with equal amounts of bromocriptine at 0800 and 2000 for 14 days. One group of mice received a high dose of bromocriptine (360 ug/0.1 ml peanut oil-/animal/day) and another group received a low dose (36 ug/day). These dosages corresponded to 12 mg/kg and 1.2 mg/kg of body weight, respectively. Controls were provided by injection of a third group of mice with peanut oil injections alone. Feed consumption (rodent laboratory chow) was monitored every 4 days and was found to be depressed somewhat in the high dosage group. Reference is made to Table 2. After 14 days of treatment, blood samples were taken at 2400 and the animals were sacrificed. Total plasma cholesterol concentration was reduced by about one-third in the high dose group. The 17% cholesterol reduction in the low dosage group was not statistically verified; a longer period of treatment may have produced significant reduction. (Abdominal fat content was also reduced by more than 50% in the high dose group even though body weight was not significantly depressed. Thus, a reduction of body fat stores accompanies a reduction of plasma cholesterol levels as a consequence of bromocriptine treatment.) A 30+% reduction in plasma cholesterol concentration, as demonstrated, is considered an extraordinary effect, able to relieve atherosclerotic symptoms

TABLE 2

Bromocriptine[1] Effects on Plasma Total Cholesterol Concentrations in White Mice.

|  | Food Consumption[2] (g/mouse/day) | Abdominal Fat (mg) | Total Cholesterol (mg/100 ml) |
|---|---|---|---|
| Controls (no bromocriptine) | 6.0 ± 0.1[3] | 240 ± 42[3] | 94.7 ± 2.5[3] |
| Low Dose Bromocriptine (36 ug/injection/day) | 5.8 ± 0.1 | 163 ± 58 | 78.7 ± 12.4 |
| High Dose Bromocriptine (360 ug/injection/day) | 5.2 ± 0.1[a] | 111 ± 41[a] | 61.5 ± 4.3[a] |

[1]Bromocriptine injections (i.p.) in peanut oil were administered daily for 14 days when the animals were sacrificed and examined for abdominal fat weight and plasma cholesterol concentrations.
[2]Food consumption was monitored every 4 days and summarized at the end of the experiment for each mouse.
[3]Mean ± Standard error of mean.
[a]Differ statistically (p < 0.01, Students' t) from the control.

EXAMPLE IV

Young (market size) female pigs (220–260 lbs) were maintained outdoors in the early fall and provided normal growing feed ad libitum. Commercial implants releasing 10 mg bromocriptine/day were inserted into an ear of each pig. Feed consumption was perhaps slightly decreased, but not significantly by bromocriptine. After 28 days of treatment, blood samples were taken at 4-hour intervals throughout a day and subsequently assayed for plasma triglyceride concentration. The triglyceride concentration in control pigs (implants containing no bromocriptine) was almost twice as high during late afternoon and early night (1600, 2000 and 2400) as during other times of day. These results are consistent with other studies in which it has been demonstrated that most hepatic lipogenesis and blood transport of lipids occurs in animals shortly before and after the beginning of the daily resting period (Ref. Meier and Fivizzani, 1974; Cincotta and Meier, 1984). Bromocriptine treatment reduced plasma triglyceride levels by about 50% during this critical lipogenic interval and by about one-third when all times of day are compared. Reference is made to Table 3.

TABLE 3

Bromocriptine[1] Effects on the Daily Rhythm of Plasma Triglyceride Concentration (mg/100 ml) in Female Pigs

| | Time of Day | | | | | |
|---|---|---|---|---|---|---|
| | 0800 | 1200 | 1600 | 2000 | 2400 | 0400 |
| Control (n = 6) | 28 ± 7[2] | 28 ± 2 | 46 ± 8 | 45 ± 9 | 63 ± 11 | 33 ± 3 |
| | | | | Daily Peak | | |
| Bromocriptine | 30 ± 3 | 23 ± 3 | 20 ± 2 | 24 ± 4 | 35 ± 3 | 32 ± 1 |

[1]Implants in ear released bromocriptine continuously (10 mg/day) for 28 days when blood was taken and examined for plasma triglyceride concentrations.
[2]Mean ± Standard error of the mean.
[3]Pigs, as other animals, have highest concentrations of plasma lipids and greatest lipogenesis shortly before and after their daily resting period.

EXAMPLE V

Bromocriptine effects on the plasma concentrations of total cholesterol and triglycerides were tested on genetically obese female Zucker rats. Bromocriptine was mixed in the food so that each rat of each group consumed about 20–25 grams rodent feed containing about 2–2.5 ug bromocriptine. The first group of rats were fed the bromocriptine-treated feed, and a second control group of normal rodent feed, or food not containing bromocriptine, beginning when the animals were 35 days old. After 5 weeks, blood samples were taken from the rats of the two groups by tail clips and analyzed for cholesterol and triglycerides. Compared with control levels, bromocriptine treatment reduced cholesterol levels by about 200% and triglyceride levels by about almost as much. Reference is made to Table 4.

TABLE 4

Bromocriptine[1] Reduces Triglyceride and Cholesterol Concentrations in the Plasma of Obese Zucker Rats

| Treatment | Cholesterol mg/100 ml | Triglycerides mg/100 ml |
|---|---|---|
| Obese Controls | 450 | 1600 |
| Bromocriptine | 150 | 575 |

[1]Bromocriptine was provided mixed with the food (about 2 mg. bromocriptine/day) which was supplied ad libitum for 5 weeks when blood samples were taken for analysis of plasma total cholesterol and triglyceride concentrations.
[2]Mean ± Standard Error.
[3]Differ from controls (p < 0., Students t).

EXAMPLE VI

The following describes tests conducted with four groups of Wistar rats (mean wt. 83 g), viz. Groups A, B, C and D, to wit:

A. Four male Wistar rats, as a control group, were maintained for 6 months on regular rat chow (Purina) and water fed ad libitum (one rat died during the period).

B. Four rats were maintained for 4 months on a heavy lipid diet (10% cholesterol, 30% saturated fat), and thereafter given bromocriptine (daily dosage: 1 mg/kg of body weight) for an additional 2 months along with the heavy lipid diet.

C. Four rats were maintained on both the heavy lipid diet (10% cholesterol, 30% saturated fat) and bromocriptine (daily dosage: 1 mg/kg of body weight) over a six month period.

D. Four rats were on the heavy lipid diet (10% cholesterol, 30% saturated fat) over a period of 4 months, and then sacrificed. (One rat died during the period.)

The coronary arteries and aortas of the rats were harvested and histologically prepared by H & E technique to maximize plaque contact with elastic fibers and smooth muscle layers.

Heart tissue was examined to detect pathological change.

The results were as follows:

A. All sections were normal. No distinctive fat deposition was found in either tunica intima or tunica media.

B. All sections demonstrated a marked reduction in fat deposits compared to animals fed the high fat diet for 4 months (Group D) and demonstrated only a minimal retention of lipid deposits in the tunica media. The tunica intima was unaffected.

C. All sections were similar to Group A. No definitive fat deposits were detected in either the tunica media or tunica intima.

D. All sections showed heavy lipid deposits among the elastic elements of the tunica media. Tunica intima was thickened.

Having described the invention, what is claimed is:

1. A method of therapeutically reducing the level of cholesterol in the blood of a vertebrate animal diagnosed as having excessive total plasma cholesterol which comprises administering to said vertebrate animal an effective dosage of a prolactin-inhibiting compound sufficient to inhibit prolactin secretion and reduce the level of cholesterol in the blood by at least 15 percent.

2. A method of therapeutically reducing the level of triglycerides in the blood of a vertebrate animal diagnosed as having excessive total plasma triglycerides which comprises administering to said vertebrate animal an effective dosage of a prolactin-inhibiting compound sufficent to inhibit prolactin secretion and reduce the level of triglycerides in the blood by at least 15 percent.

3. A method of therapeutically reducing the levels of cholesterol and triglycerides in the blood of a vertebrate animal diagnosed as having excessive total plasma cholesterol and triglycerides which comprises administering to said vertebrate animal an effective dosage of a prolactin-inhibiting compound sufficient to inhibit prolactin secretion and reduce the cholesterol and triglyceride levels in the blood by at least 15 percent.

4. A method of suppressing and reducing the level of lipid plaques formed in the walls of the blood vessels of a vertebrate animal diagnosed as having an atherosclerotic condition which comprises administering to said animal an effective dosage of a prolactin-inhibiting compound sufficient to inhibit prolactin secretion and decrease the total plasma cholesterol and total triglyceride levels in the blood of the animal over a period of time sufficient to suppress and reduce the formation of lipid plaques in the walls of the blood vessels of the animal.

5. The method of claim 4 wherein the dosage is administered over a period of at least about 25 days.

6. The method of claim 5 wherein the period of treatment ranges from about 90 days to about 180 days.

7. The method of claim 5 wherein the amount of plaque in the walls of the blood vessels of the animal is reduced by at least 15 percent.

8. The method of claim 4 wherein the dosage is administered over a period of at least 90 days, and the amount of plaque in the walls of the blood vessel of the animal is reduced by at least 15 percent.

9. The method of claim 4 wherein the prolactin-inhibiting compound is 2-bromo-alpha-ergocryptine or its salts formed from pharmaceutically acceptable acids.

10. The method of claim 4 wherein the prolactin-inhibiting compound is 2-bromo-alpha-ergocryptine or its salts formed from pharmaceutically acceptable acids, and the dosage of said prolactin-inhibiting compound is administered over a period of at least 25 days.

11. The method of claim 10 wherein the daily dosage of the prolactin-inhibiting compound ranges from about 0.02 mg/kg of body weight to about 6 mg/kg of body weight.

12. The method of claim 4 wherein the prolactin-inhibiting compound is selected from the group consisting of 6-methyl-8 beta-carbobenzyloxy-aminoethyl-10 alpha-ergoline; 1,6-dimethyl-8 beta-carbobenzyloxyaminomethyl-10 alpha-ergoline; 8-acylaminoergolenes; ergocornine; 9,10-dihydroergocornine; and D-2-halo-6-alkyl-8-substituted ergolines.

13. The method of claim 4 wherein the dosage of the prolactin-inhibiting compound is administered to a human, the dosage ranges from about 2.0 mg/100 kg of body weight to about 10 mg/100 kg of body weight, and the dosage is administered over a period of at least 25 days.

14. The method of claim 13 wherein the dosage of said prolactin-inhibiting compound is administered over a period of from about 90 days to about 120 days.

15. The method of claim 13 wherein the amount of plaque in the walls of the blood vessels of the human as a result of the treatment is reduced by at least 15 percent, based on weight.

16. The method of claim 13 wherein the amount of plaque in the walls of the blood vessels of the human as a result of the treatment is reduced by at least 50 percent, based on weight.

17. The method of claim 13 wherein the prolactin-inhibiting compound is 2-bromo-alpha-ergocryptine or its salts formed from pharmaceutically acceptable acids.

18. The method of claim 13 wherein the prolactin-inhibiting compound is selected from the group consisting of 6-methyl-8 beta-carbobenzyloxy-aminoethyl-10 alpha-ergoline; 1,6-dimethyl-8 beta-carbobenzyloxyaminomethyl-10 alpha-ergoline; 8-acylaminoergolenes; ergocornine; 9,10-dihydroergocornine; and D-2-halo-6-alkyl-8-substituted ergolines.

* * * * *